United States Patent
Iwamoto et al.

(10) Patent No.: US 11,692,006 B2
(45) Date of Patent: Jul. 4, 2023

(54) METHOD OF SOLID-PHASE NUCLEIC ACID SYNTHESIS AND SOLUTION COMPOSITION FOR SOLID-PHASE NUCLEIC ACID SYNTHESIS

(71) Applicant: Nitto Denko Corporation, Osaka (JP)

(72) Inventors: Masafumi Iwamoto, Osaka (JP); Tsuyoshi Mukobata, Osaka (JP); Akira Yokouchi, Osaka (JP)

(73) Assignee: Nitto Denko Corporation, Osaka (JP)

(*) Notice: Subject to any disclaimer, the term of this patent is extended or adjusted under 35 U.S.C. 154(b) by 540 days.

(21) Appl. No.: 16/627,718

(22) PCT Filed: Jul. 4, 2018

(86) PCT No.: PCT/JP2018/025366
§ 371 (c)(1),
(2) Date: Dec. 30, 2019

(87) PCT Pub. No.: WO2019/009329
PCT Pub. Date: Jan. 10, 2019

(65) Prior Publication Data
US 2021/0206797 A1 Jul. 8, 2021

(30) Foreign Application Priority Data
Jul. 5, 2017 (JP) .............................. JP2017-132118

(51) Int. Cl.
| | | |
|---|---|---|
| C07H 21/04 | (2006.01) | |
| C07H 19/073 | (2006.01) | |
| C07H 19/207 | (2006.01) | |
| C07K 1/04 | (2006.01) | |

(52) U.S. Cl.
CPC ........... C07H 21/04 (2013.01); C07H 19/073 (2013.01); C07H 19/207 (2013.01); C07K 1/042 (2013.01)

(58) Field of Classification Search
None
See application file for complete search history.

(56) References Cited

U.S. PATENT DOCUMENTS

| | | | |
|---|---|---|---|
| 6,538,128 B1 | 3/2003 | Zhang et al. | |
| 7,273,933 B1 * | 9/2007 | Krotz ..................... | C07H 21/00 536/25.31 |

FOREIGN PATENT DOCUMENTS

WO  WO 99/43694  9/1999

OTHER PUBLICATIONS

Donga et al., Journal of Organic Chemistry, vol. 71, No. 20, Sep. 2006. (Year: 2006).*

Bonora et al., A Liquid-Phase Process Suitable for Large-Scale Synthesis of Phosphorothioate Oligonucleotides. Organic Process Res. and Dev. 2000, 4:225-231.
Damha et al., Chemical Synthesis of Branched RNA: Novel trinucleoside diphosphates containing vicinal 2'-5' and 3'-5' phosphodiester linkages. Tetrahedron Ltts. 1985, 26(40):4839-4842.
Damha et al., Synthesis and Spectroscopic Analysis of Branched RNA Fragments: Messenger RNA Splicing Intermediates. J Org Chem. 1988, 53:3710-3722.
Donga et al., A novel approach to oligonucleotide synthesis using an imidazolium ion tag as a soluble support. J Org Chem. 2006, 71(20):7907-7910.
Gaffney et al., Liquid-phase Synthesis of 2'-Methyl-RNA on a Homostar Support through Organic-Solvent Nanofiltration. Chemistry. 2015, 21(26):9535-9543.
De Koning et al., Simple and Efficient Solution-Phase Synthesis of Oligonucleotides Using Extractive Work-Up. Org Process Res Develop. 2006, 10(6):1238-1245.
Kungurtsev et al., Solution-Phase Synthesis of Short Oligo-2/-deoxyribonucleotides by Using Clustered Nucleosides as a Soluble Support. Eur J Org Chem. 2013, 29:6687-6693.
Molina et al., Solution phase synthesis of short oligoribonucleotides on a precipitative tetrapodal support. Beilstein J Org Chem. 2014, 10:2279-2285.
Nonoyama et al., Ordered Nanopattern Arrangement of Gold Nanoparticles on β-sheet Peptide Templates through Nucleobase Pairing. ACS Nano. 2011, 5(8):6174-6183.
International Search Report and Written Opinion dated Oct. 2, 2018 for Application No. PCT/JP2018/025366 in 13 pages.
Hearing Notice in Indian Application No. 202017003623, dated Dec. 15, 2021.
Office Action issued in Indian Application No. 202017003623, dated Dec. 30, 2020.
Office Action issued in Korean Application No. 10-2020-7001239, dated Dec. 29, 2020.
Final Rejection issued in Korean Application No. 10-2020-7001239, dated Aug. 13, 2021.
Office Action issued in Japanese Application No. 2017-132118, dated Jun. 8, 2021 (translation).
Decision of Refusal issued in Japanese Application No. 2017-132118, dated Sep. 14, 2021.

(Continued)

*Primary Examiner* — Traviss C McIntosh, III
(74) *Attorney, Agent, or Firm* — Knobbe, Martens, Olson & Bear, LLP

(57) ABSTRACT

This invention is intended to discover a novel solvent that can be used as an alternative to toluene in the step of deprotection in the method of solid-phase nucleic acid synthesis. With the use of such novel solvent, various problems caused by the use of toluene are dissolved.
This invention is also intended to provide a method of solid-phase nucleic acid synthesis in which protected nucleoside phosphoramidites in which a protective group is bonded to a hydroxyl group at the 5'position or the 3' position of a nucleoside are sequentially bound on a solid phase carrier, where a reaction of removing the protecting group from the protected nucleoside phosphoramidite is carried out in a solution comprising an acid with a pKa of 0.2 to 0.8 and acetonitrile.

7 Claims, No Drawings

Specification includes a Sequence Listing.

(56) References Cited

OTHER PUBLICATIONS

Written Opinion issued in International Application No. PCT/JP2018/025366, dated Oct. 2, 2018 (translation).
Chemistry and Education, 2009, vol. 57, No. 7, p. 346-347.
Office Action in Japanese Application No. 2017-132118 dated Jun. 8, 2021.
Valencia, Drochss P., et al., "Self-decarboxylation of trichloroacetic acid redox catalyzed by trichloroacetate ions in acetonitrile solutions", Org. Biomol. Chem., 2013, 11, 318-325.
Extended European Search Report in Application No. EP 18828435.0, dated Mar. 29, 2021.
Office Action issued in Chinese Application No. 201880044737.X, dated Sep. 2, 2022.

\* cited by examiner

METHOD OF SOLID-PHASE NUCLEIC ACID SYNTHESIS AND SOLUTION COMPOSITION FOR SOLID-PHASE NUCLEIC ACID SYNTHESIS

TECHNICAL FIELD

The present invention relates to a method of solid-phase nucleic acid synthesis in which a solid-phase support comprising, for example, glass beads or porous resin beads, is used to synthesize nucleic acids on such solid-phase support and a solution composition used for the method of solid-phase nucleic acid synthesis.

BACKGROUND ART

A method of solid-phase nucleic acid synthesis is also referred to as a phosphoramidite method in which nucleotide chains are synthesized on a solid-phase support comprising glass or porous resin, so that an oligonucleotide or polynucleotide comprising a desired sequence is synthesized. In such method of synthesis, specifically, a nucleoside with the 3'-OH group derivatized with phosphoramidite and the 5'-OH group protected with a dimethoxytrytyl group (a protecting group) is extended via coupling of nucleotides in the 5' direction.

More specifically, a method of synthesis comprises: a step of deprotection comprising elimination of a protecting group from a nucleoside using a trichloroacetic acid/dichloromethane solution or a dichloroacetic acid/toluene solution; a step of coupling comprising allowing the 5' end of the deprotected nucleoside to react with a phosphoramidite group of the adjacent nucleoside; a step of capping comprising acetylation, so as to prevent an unreacted 5'—OH group from reacting in the subsequent step of coupling; and a step of oxidation comprising oxidizing a bond between adjacent nucleosides, so as to convert trivalent phosphorus to pentavalent phosphate ester. By repeating the step of deprotection, the step of coupling, the step of capping, and the step of oxidation in that order, an oligonucleotide or polynucleotide comprising a desired sequence is synthesized.

In a method of solid-phase nucleic acid synthesis, after the completion of all steps of synthesis, the final process of detritylation is carried out, followed by eliminating from the solid-phase support and removing a protecting group bound to a side chain. The synthesized oligonucleotide or polynucleotide is subjected to treatment, such as cleavage, production, leaching concentration, and lyophillization, in accordance with conventional techniques.

As disclosed in Patent Documents 1 and 2, in general, a deprotection reaction involves the use of a 3% to 10% dichloroacetic acid (DCA)/toluene solution. Toluene is generally used as a synthetic raw material for a dye, an aroma chemical, gunpowder (TNT), an organic pigment, synthetic cresol, a sweetening agent, a bleaching agent, TDI, terephthalic acid, a synthetic fiber, and a plasticizer; a benzene raw material; a xylene raw material; a petroleum refiner; a pharmaceutical product; a paint or an ink solvent; and the like. Toluene is a harmful organic solvent in a working environment. When toluene is used as a solvent at the industrial level, for example, it is necessary to handle toluene with extra care and recover the same with a high yield.

When toluene is used in the step of deprotection in the method of solid-phase nucleic acid synthesis, toluene is occasionally carried over to the subsequent step of coupling and the like (i.e., carry-over). Even if a step of washing a solid-phase support is carried out after the step of deprotection, for example, it is very difficult to completely prevent toluene carry-over.

In the step of coupling and other steps, an organic solvent other than toluene, such as acetonitrile solvent, is used. If toluene is carried over to the step of coupling and other steps, other than the step of deprotection, a mixture of acetonitrile used in the step of coupling and other steps with toluene will be recovered. It is very difficult to separate acetonitrile from a mixture of acetonitrile with toluene with high purity. Accordingly, re-use of acetonitrile at high purity necessitates a very cost-consuming process.

Non-Patent Document 1 discloses a method of liquid-phase nucleic acid synthesis in which a deprotection reaction is carried out using a solution of 3% by mass trifluoroacetic acid in acetonitrile. In the method of solid-phase nucleic acid synthesis, however, a deprotection reaction did not proceed with the use of acetonitrile as an organic solvent, as disclosed in Patent Document 1. That is, acetonitrile is not used in methods of solid-phase nucleic acid synthesis.

PRIOR ART DOCUMENTS

Patent Documents

Patent Document 1: U.S. Pat. No. 6,538,128
Patent Document 2: U.S. Pat. No. 7,273,933

Non-Patent Documents

Non-Patent Document 1: J. Org. Chem., Vol. 71, No. 20, pp. 7907-7910, 2006

SUMMARY OF THE INVENTION

Objects to Be Attained by the Invention

As described above, use of toluene in methods of solid-phase nucleic acid synthesis was problematic in terms of hazardousness imposed on the environment due to toluene, cost required for toluene recovery, and difficulty in separation from other organic solvents. Under the above circumstances, the present invention is intended to discover a novel solvent that can be an alternative to toluene in the step of deprotection in a method of solid-phase nucleic acid synthesis. Also, the present invention is intended to provide an excellent method of solid-phase nucleic acid synthesis involving the use of such novel solvent, which had overcome various problems caused by the use of toluene, and a solution composition used for such method of solid-phase nucleic acid synthesis.

Means for Attaining the Objectives

The present inventors have conducted concentrated studies in order to attain the above objects. As a result, they discovered that a deprotection reaction aimed at elimination of a protecting group from a nucleoside would proceed with the use of a solution comprising an acetonitrile in combination with an acid at a predetermined strength. This has led to the completion of the present invention. The present invention is as follows.

[1] A method of solid-phase nucleic acid synthesis in which protected nucleoside phosphoramidites in which a protective group is bonded to a hydroxyl group at the 5 'position or the 3' position of a nucleoside are sequentially bound on a solid phase carrier, comprising a step of deprotection performing a reaction of removing the protecting group from the protected nucleoside phosphoramidite in a solution comprising an acid with a pKa of 0.2 to 0.8 and acetonitrile.

[2] The method of solid-phase nucleic acid synthesis according to [1], wherein the protecting group is a trytyl group or its derivative or a 9-phenylxanthen-9-yl group or its derivative.

[3] The method of solid-phase nucleic acid synthesis according to [1], wherein the acid is trichloroacetic acid and/or trifluoroacetic acid.

[4] The method of solid-phase nucleic acid synthesis according to [1], wherein the solid-phase support comprises porous resin beads.

[5] The method of solid-phase nucleic acid synthesis according to [4], wherein the step of deprotection is carried out by allowing the solution to flow through a column filled with the porous resin beads.

[6] The method of solid-phase nucleic acid synthesis according to [5], wherein a flow rate of the solution is 400 to 2,000 cm/h.

[7] The method of solid-phase nucleic acid synthesis according to [5], wherein a length of the layer comprising porous resin beads introduced into the column is 4 to 50 cm in a flow pass direction, provided that the length is determined when the porous resin beads are swollen with the solution.

[8] A solution composition for solid-phase nucleic acid synthesis comprising an acid with a pKa of 0.2 to 0.8 and acetonitrile, which is used for a reaction of removing a protecting group from a protected nucleoside phosphoramidite in the method of solid-phase nucleic acid synthesis in which protected nucleoside phosphoramidites in which a protective group is bonded to a hydroxyl group at the 5 'position or the 3' position of a nucleoside are sequentially bound on a solid phase carrier.

[9] The solution composition for solid-phase nucleic acid synthesis according to [8], wherein the acid is trichloroacetic acid and/or trifluoroacetic acid.

This description contains part or all of the contents as disclosed in the description and/or drawings of Japanese Patent Application No. 2017-132118, based on which the present application claims priority.

Effects of the Invention

The method of solid-phase nucleic acid synthesis according to the present invention involves the use of acetonitrile instead of toluene as an organic solvent in a reaction of removing a protecting group from a nucleoside. According to the method of solid-phase nucleic acid synthesis according to the present invention, various problems, such as hazardousness imposed on the environment due to the use of toluene and an increased recovery cost, can be avoided.

The solution composition for solid-phase nucleic acid synthesis according to the present invention comprises acetonitrile instead of toluene as an organic solvent used in a reaction of removing a protecting group from a nucleoside. With the use of the solution composition for solid-phase nucleic acid synthesis according to the present invention, various problems, such as hazardousness imposed on the environment due to the use of toluene and an increased recovery cost, can be avoided.

EMBODIMENTS FOR CARRYING OUT THE INVENTION

Hereafter, the method of solid-phase nucleic acid synthesis and the solution composition for solid-phase nucleic acid synthesis according to the present invention are described in detail.

In the method of solid-phase nucleic acid synthesis, a nucleotide chain comprising nucleotide units linked to each other via phophodiester bonds is synthesized on a solid-phase support. In the method of solid-phase nucleic acid synthesis, a nucleotide chain is synthesized with the use of a protected nucleoside phosphoramidite comprising a protecting group bound to a hydroxyl group at position 5' or 3' of a nucleoside and a hydroxyl group at position 3' derivatized with phosphoramidite. When a nucleotide chain is synthesized by the method of the present invention, nucleotide units may be linked one by one, or a plurality of nucleotide units may be simultaneously linked with the use of a protected nucleoside phosphoramidite comprising a plurality of nucleotide units. While both methods comprise formation of phophodiester bonds between adjacent nucleotide units, a step of reaction of removing a protecting group from protected nucleoside phosphoramidite in advance. A step of removing a protecting group from protected nucleoside phosphoramidite is referred to as a step of deprotection.

In the method of solid-phase nucleic acid synthesis according to the present invention, the step of deprotection is carried out with the use of a solution comprising an acid with a pKa of 0.2 to 0.8 and acetonitrile (i.e., a solution composition for solid-phase nucleic acid synthesis). In other words, a reaction of removing a protecting group from protected nucleoside phosphoramidite is carried out in a solution comprising an acid with a pKa of 0.2 to 0.8 and acetonitrile. In a conventional method of solid-phase nucleic acid synthesis, a deprotection reaction was carried out with the use of a solution of dichloroacetic acid (with a pKa of 1.25) in toluene (a solution of 3% to 10% dichloroacetic acid). In the method of solid-phase nucleic acid synthesis according to the present invention, acetonitrile is used instead of toluene. Accordingly, an acid having a higher acidity than dichloroacetic acid and a strength that would not result in degradation of a nucleotide chain is used. For example, such acid has a pKa of 0.2 to 0.8.

The solution composition for solid-phase nucleic acid synthesis according to the present invention is a solvent composition used for the step of deprotection described above, which is a solution comprising an acid with a pKa of 0.2 to 0.8 and acetonitrile.

Specific examples of acids with a pKa of 0.2 to 0.8 include trichloroacetic acid (a pKa of 0.66), trifluoroacetic acid (a pKa of 0.2), benzenesulfonic acid (a pKa of 0.7), pyrazine (a pKa of 0.37), and 2,4,6-trinitrophenol (a pKa of 0.42).

The step of deprotection in the method of solid-phase nucleic acid synthesis according to the present invention can involve the use of one or more acids with a pKa of 0.2 to 0.8 selected from among those exemplified above. When a plurality of acids are used in combination, a plurality of acids selected from among acids with a pKa of 0.2 to 0.8 may be used in combination. Alternatively, at least one acid with a pKa of 0.2 to 0.8 may be used in combination with one or more acids with a pKa outside the range described above (an acid may be with a pKa higher than the upper limit or lower than the lower limit the range described above). Also, two or more acids with a pKa of 0.2 to 0.8 may be used in combination. Acids with a pKa outside such range are not particularly limited, and examples thereof include dichloroacetic acid (a pKa of 1.25), 2-aminoethanesulfonic acid (a pKa of 1.5), and 2-pyridyl carboxylic acid (a pKa of 0.99).

When a plurality of types of acids are used in combination, as described above, it is preferable to select an acid that allows a reaction of removing a protecting group to proceed in an acetonitrile solution and nucleic acid synthesis to proceed without degrading a nucleotide chain. Whether or not a reaction of removing a protecting group proceeds in an acetonitrile solution can be evaluated by, for example, adding a nucleotide chain comprising a dimethyltrytyl group (a protecting group) in an acetonitrile solution containing an acid to be evaluated, and evaluating removal of a dimethyltrytyl group based on the development of color derived from the dimethyltrytyl group after the elapse of a given period of time. Whether or not nucleic acid synthesis proceeds without degrading a nucleotide chain can be evaluated by synthesizing a particular nucleic acid sequence in the presence of an acetonitrile solution containing an acid to be evaluated and determining the purity (%) of the nucleic acid synthesized.

In the step of deprotection, the concentration of an acid with a pKa of 0.2 to 0.8 is not particularly limited. For example, it can be 3% to 10% by mass, preferably 3% to 9% by mass, and more preferably 5% to 7% by mass. As described above, the acid concentration can adequately be determined in accordance with the efficiency for the reaction of removing a protecting group and/or the efficiency for nucleic acid synthesis.

When trichloroacetic acid is used as an acid with a pKa of 0.2 to 0.8, in particular, the concentration of trichloroacetic acid in an acetonitrile solution can be, for example, 5% to 9% by mass, preferably 6% to 8% by mass, and more preferably 7% by mass. When trifluoroacetic acid is used as an acid with a pKa of 0.2 to 0.8, also, the concentration of trifluoroacetic acid in an acetonitrile solution can be, for example, 3% to 9% by mass, preferably 5% to 7% by mass, and more preferably 6% by mass.

A protecting group is not particularly limited, and examples thereof include a trityl-based protecting group and/or a silyl-based protecting group that can be eliminated by an acid. The term "trityl-based protecting group" refers to a trytyl group or a derivative thereof. A protecting group can also be a 9-phenylxanthen-9-yl group or a derivative thereof. Examples of protecting groups that can be used include, but are not limited to, trytyl, monomethoxytrityl, dimethoxytrityl, 9-phenylxanthen-9-yl, and 9-p-methoxyphenylxanthen-9-yl, as disclosed in U.S. Pat. No. 6,538,128.

A specific example of a trityl-based protecting group is a trytyl group that can be substituted with any substituent (e.g., a substituent selected from among a $C_{1-6}$ alkoxy group, a $C_{1-6}$ alkyl group, and a halogen atom (two or more substituents may together form a ring)). More specific examples include a trytyl group (Tr), a monomethoxy trytyl group (e.g., a 4-methoxy trytyl group (MMTr)), a dimethoxy trytyl group (e.g., a 4,4'-dimethoxy trytyl group (DMTr)), and a 9-phenylxanthen-9-yl group (a pixyl group), with a 4,4'-dimethoxy trytyl group (DMTr) being preferable. In particular, a protecting group is preferably a trityl-based protecting group, with a dimethoxy trytyl group (DMT) being more preferable.

Further specifically, an example of a silyl-based protecting group is a silyl group trisubstituted with any substituent (e.g., a substituent selected from among a $C_{1-6}$ alkoxy group, a $C_{1-6}$ alkyl group, and a phenyl group). Specific examples thereof include a trimethylsilyl group, a triethylsilyl group, an isopropyl dimethylsilyl group, a tert-butyl dimethylsilyl group, a dimethyl methoxysilyl group, a methyldimethoxysilyl group, and a tert-butyl diphenylsilyl group, with a trimethylsilyl group being preferable.

As a 9-phenylxanthen-9-yl group (a pixyl group) or a derivative thereof (e.g., a 4'-dimethoxypixyl), for example, functional groups represented by formulae below can be used as disclosed in Nucleosides, Nucleotide and Nucleic Acids, 30: 12-19, 2011.

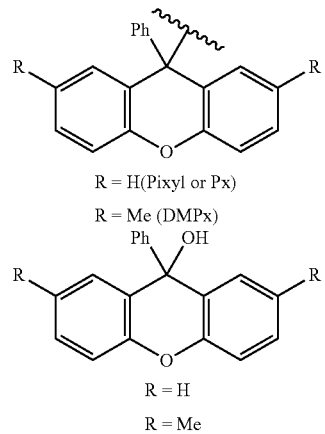

R = H(Pixyl or Px)
R = Me (DMPx)

R = H
R = Me

The method of solid-phase nucleic acid synthesis according to the present invention can adopt various conventional methods of synthesis, provided that the method comprises a step of deprotection involving the use of a solution containing an acid with a pKa of 0.2 to 0.8 and acetonitrile, as described above. Specifically, nucleotides are allowed to successively bind to a nucleoside, nucleotide, or oligonucleotide bound to a solid-phase support, so as to obtain an extended oligonucleotide. Examples of reactions of nucleic acid synthesis include the H-phosphonate method, the phosphoester method, and the solid-phase phosphoramidite method. The solid-phase phosphoramidite method is particularly preferable because the ability of nucleic acid synthesis is high and a high-purity nucleic acid can be obtained.

In order to perform a reaction of nucleic acid synthesis by the solid-phase phosphoramidite method, at the outset, a reaction column is filled with a solid-phase support, or a reaction column filled with a solid-phase support is prepared. In the reaction of nucleic acid synthesis, subsequently, a step of deprotection is performed by introducing an acetonitrile solution comprising the acid with a pKa of 0.2 to 0.8 into a reaction column filled with a solid-phase support.

A solid-phase support is not particularly limited, provided that the 3' terminal side of a nucleic acid to be synthesized can be immobilized via a linker or directly to the support. Examples thereof include a glass-based porous support and porous resin supports, such as a polystyrene-based porous support and an acrylamide-based porous support. The use of a porous resin support is particularly preferable, and the use of a polystyrene-based porous support is further preferable.

A "polystyrene-based porous support" is a porous support made of resin mainly composed of constitutional units derived from styrene or a derivative thereof. A polystyrene-based porous support comprising an amino group and/or a hydroxy group is particularly preferable. Examples of polystyrene-based porous supports include a porous support comprising styrene-hydroxystyrene-divinyl benzene-based copolymer particles (see JP 2005-097545 A, JP 2005-325272 A, and JP 2006-342245 A) and a porous support comprising a styrene-(meth)acrylonitrile-hydroxystyrene-divinyl benzene-based copolymer (see JP 2008-074979 A).

An "acrylamide-based porous support" is a porous support made of resin mainly composed of constitutional units derived from acrylamide or a derivative thereof. An acrylamide-based porous support comprising an amino group and/or a hydroxy group is particularly preferable, and an acrylamide-based porous support comprising a hydroxy group is further preferable.

In addition, an example of a solid-phase support is a support comprising a copolymer of a first aromatic monovinyl compound, a divinyl compound, (meth)acrylonitrile, and a second aromatic monovinyl compound, as disclosed in JP Patent No. 5,479,828. The term "first aromatic monovinyl compound" refers to styrene or a substitute thereof. The term "divinyl compound" refers to an aromatic divinyl compound, di(meth)acrylic acid ester, or a substitute thereof. The term "(meth)acrylonitrile" refers to "acrylonitrile," "methacrylonitrile," or "both acrylonitrile and methacrylonitrile." The term "second aromatic monovinyl compound" refers to styrene comprising a "functional group capable of binding to a carboxyl group via a dehydration condensation reaction" or a substitute thereof.

A form of a solid-phase support is not particularly limited, and it may be in any of a plate, particulate, fibrous, or other form. A solid-phase support preferably comprises beads (particles) because such support can be introduced into a reaction column with enhanced efficiency and such reaction container is less likely to be damaged. The term "bead" does not strictly refer to a spherical form. For example, a bead may be in an approximately spherical form, such as an oval form, or in an atypical form, such as a polyhedral, cylindrical, or sugar-plum-shaped form.

In particular, a resin support, such as a porous resin bead support, is likely to swell in toluene but it is relatively less likely to swell in acetonitrile. In the method of solid-phase nucleic acid synthesis according to the present invention, the step of deprotection involves the use of acetonitrile as an organic solvent instead of toluene, which is used in accordance with a conventional technique. Accordingly, a degree of swelling can be reduced with the use of a porous resin support. In the method of solid-phase nucleic acid synthesis according to the present invention, accordingly, the use of a porous resin support is preferable, and the use of a porous resin bead support is more preferable. Since a degree of swelling can be reduced with the use of a porous resin bead support, pressure elevation can be reduced when a solution is allowed to flow through the reaction column filled with such support.

In the step of deprotection in the method of solid-phase nucleic acid synthesis according to the present invention, in other words, an acetonitrile solution can be allowed to flow through a reaction column filled with porous resin beads at a faster flow rate than a toluene solution when it is allowed to flow through the column at the same pressure. It should be noted that there is a permissible upper limit for a pressure that can be applied to the reaction column. When a toluene solution is used, accordingly, a flow rate equivalent to the flow rate that is employed for an acetonitrile solution may not be employed.

In the method of solid-phase nucleic acid synthesis according to the present invention, the step of deprotection can be carried out at an acetonitrile solution flow rate of 400 cm/h or more in a reaction column (column length: 10 cm) in which the maximal flow rate for a toluene solution is 400 cm/h. With the use of an acetonitrile solution as described above, specifically, a degree of porous resin bead swelling can be reduced, the pressure within the reaction column would not reach its permissible upper limit even if the flow rate of an acetonitrile solution is 400 cm/h or more, and an acetonitrile solution is thus allowed to flow through the column. The term "column length" used herein refers to a length of a layer comprising porous resin beads that had been introduced into the reaction column, which is indicated by a numerical value determined when porous resin beads are swollen with a solution.

In the method of solid-phase nucleic acid synthesis according to the present invention, in particular, a step of deprotection can be carried out by allowing an acetonitrile solution to flow through a reaction column (column length: 4 cm) filled with porous resin beads at the flow rate of 2,000 cm/h. In the method of solid-phase nucleic acid synthesis according to the present invention, specifically, an acetonitrile solution can be allowed to flow through the column at the flow rate of 400 to 2,000 cm/h, preferably 800 to 2,000 cm/h, and more preferably 1,200 to 2,000 cm/h.

As described above, when porous resin beads is used as a solid-phase support, a flow rate of an acetonitrile solution can be set relatively higher than the flow rate that can be employed when a toluene solution is used in accordance with a conventional technique. In the method of solid-phase nucleic acid synthesis according to the present invention, accordingly, the time required for the step of deprotection can be reduced, side reactions other than the reaction of removing a protecting group caused by an acid can be prevented from occurring, and the purity and the yield of the synthesized nucleic acids can be enhanced.

In addition, the method of solid-phase nucleic acid synthesis according to the present invention involves the use of an acetonitrile solution in the step of deprotection as described above. This can suppress swelling of porous resin beads introduced into the reaction column, and the amount of porous resin beads to be introduced into the reaction column can be thus increased. When the solution is allowed to flow through a reaction column at the permissible upper limit of the pressure, for example, the amount of porous resin beads introduced into the column can be increased according to the method of solid-phase nucleic acid synthesis according to the present invention; that is, a column length can be increased, compared with the case where a toluene solution is used. For example, even if the upper limit of the column length is 10 cm (flow rate: 400 cm/h) in the case that a toluene solution is used, a column length can be 4 to 50 cm according to the method of solid-phase nucleic acid synthesis of the present invention.

As described above, when porous resin beads is used as a solid-phase support, a column length of a reaction column can be increased, compared with the case where a conventional toluene solution is used. According to the method of solid-phase nucleic acid synthesis according to the present invention, accordingly, more reactions of nucleic acid synthesis can be carried out in a single lot, and productivity can be significantly enhanced.

Any conventional porous resin beads can be used without particular limitations. An average particle diameter of porous resin beads is not particularly limited. When an average particle diameter measured via laser diffraction (a scattering method) is smaller than 1 μm, disadvantageously, a back pressure may become excessively high or a flow rate may become slower when beads are introduced into the column. When an average particle diameter is larger than 1,000 μm, in contrast, gaps among beads become increased when beads are introduced into the column That is, it may become difficult to efficiently introduce beads into a column with a certain volume. Accordingly, an average particle diameter of porous resin beads is preferably 1 to 1,000 μm, more preferably 5 to 500 μm, and further preferably 10 to 200 μm.

A specific surface area of porous resin beads measured by the multiple-point BET method is not particularly limited. When a specific surface area is smaller than 0.1 mm$^2$/g, however, a degree of swelling in an organic solvent may become excessively low, and a reaction of synthesis may become less likely to occur. When a specific surface area is larger than 500 m$^2$/g, in contrast, a pore diameter becomes smaller, and a reaction of synthesis may become less likely to occur. Accordingly, a specific surface area of porous resin beads is preferably 0.1 to 500 m$^2$/g, more preferably 10 to 300 m$^2$/g, and further preferably 50 to 200 m$^2$/g.

In addition, an average pore diameter of porous resin beads measured by the mercury intrusion method is not particularly limited. When a pore diameter is excessively small, however, a field of a reaction of synthesis may become smaller, a reaction of interest may become less likely to occur, or the length of nucleotides may become shorter than the number of interest. When an average pore diameter of porous resin beads is excessively large, in contrast, contacts between hydroxy groups and substances related to the reaction may become reduced on the bead surface, which is a reaction field, and an yield may become lowered. Accordingly, an average pore diameter of porous resin beads is preferably 1 to 200 nm, more preferably 5 to 100 nm, and further preferably 20 to 70 nm.

Porous resin beads preferably comprise a functional group that contributes to nucleic acid synthesis. A functional group "that contributes to nucleic acid synthesis" can serve as a point of initiation for the nucleic acid synthesis, and it is capable of linker addition. Specific examples thereof include an amino group and a hydroxy group. Specific examples of porous resin beads include those described in JP 2011-088843 A and JP 2013-177371 A. In addition, polystyrene particles with low degrees of swelling, which are commercialized as NittoPhase (Registered trademark) (Nitto Denko Corporation), can be used as porous resin beads. According to the method of solid-phase nucleic acid synthesis using NittoPhase (Registered trademark), a peak area arising from impurities can be small, and a high yield and a high purity can be achieved with certainty in a large scale ranging from laboratory scale to mass-synthesis systems.

In the reaction of nucleic acid synthesis by the solid-phase phosphoramidite method, subsequently, an acid with a pKa of 0.2 to 0.8 is removed from the reaction system by introducing a wash solution into the reaction column (the step of washing) after the step of deprotection. In the method of solid-phase nucleic acid synthesis according to the present invention, the step of deprotection involves the use of an organic solvent and an acetonitrile solution used in the step of coupling and other steps described below. Accordingly, it is sufficient if an acid with a pKa of 0.2 to 0.8 can be removed from the reaction system. In the method of solid-phase nucleic acid synthesis according to the present invention, use of organic solvents (e.g., toluene) other than acetonitrile is not necessary in the step of deprotection and the subsequent step of washing. According to the method of solid-phase nucleic acid synthesis according to the present invention, accordingly, acetonitrile used in the step of deprotection and the subsequent step of washing can be recovered, purified in a simple manner, and reused.

In the reaction of nucleic acid synthesis by the solid-phase phosphoramidite method, subsequently, a step of coupling in which a nucleoside phosphoramidite activated with the aid of tetrazole or the like, which corresponds to the 3' terminus, is bound to a hydroxymethyl group, a step of capping an unreacted hydroxyl group, and a step of phosphite oxidation are successively carried out, and these steps are repeated until the target sequence is obtained. After the synthesis of the target sequence is completed, a solid-phase support is soaked in ammonia water or the like to cleave the portion linked to the nucleotide chain, and a nucleotide chain comprising the target sequence can then be obtained.

A nucleotide chain synthesized by the method of solid-phase nucleic acid synthesis is a chain compound comprising nucleotides linked to each other via phosphodiester bonds, and it comprises DNA, RNA, and the like. The term "nucleic acid" used herein refers not only to an oligonucleotide comprising a purine base, such as adenine (A) and guanine (G), and a pyrimidine base, such as thymine (T), cytosine (C), and uracil (U), but the term also refers to a modified oligonucleotide comprising such modified nucleic acid base.

EXAMPLES

Hereafter, the present invention is described in greater detail with reference to the examples, although the technical scope of the present invention is not limited to the examples below.

Example 11

In Example 1, Nitto Phase HL comprising, carried thereon, T to which a dimethyltrytyl group (a protecting group) had bound was used, and a reaction of removing a protecting group was examined using various solvents in combination with acid substances. In Example 1, acetonitrile, acetone, ethyl acetate, DMF, DMSO, hexane, methanol, and ethanol were prepared as candidate solvents. In addition, dichloroacetic acid (DCA), trichloroacetic acid (TCA), trifluoroacetic acid (TFA), p-toluenesulfonic acid (PTSA), and hydrochloric acid were prepared as acid substances.

Experimental Procedure 1

Candidate solvents were mixed with acid substances in the manner described below.
Preparation of Solutions of Candidate Solvents Containing 3% DCA:
 DCA (1.5 ml) was added to a 50-ml volumetric flask using a measuring pipette. The 50-ml volumetric flask was filled with the solutions.
Preparation of 50% Mixed Solutions of Toluene and Candidate Solvents Containing 3% DCA:
 DCA (1.5 ml) was added to a 50-ml volumetric flask using a measuring pipette. The 50-ml volumetric flask was filled with the mixed solutions of toluene and candidate solvents at 1:1.
Preparation of Solutions of Candidate Solvents Containing 9% TCA:
 TCA (1.5 ml) was added to a 50-ml volumetric flask using a measuring pipette. The 50-ml volumetric flask was filled with the solutions.
Preparation of Solutions of Candidate Solvents Containing 3% TFA:
 TFA (1.5 ml) was added to a 50-ml volumetric flask using a measuring pipette. The 50-ml volumetric flask was filled with the solutions.
Preparation of Solutions of Candidate Solvents Containing PTSA:
 PTSA (951.3 mg) was added to a 50-ml volumetric flask. The 50-ml volumetric flask was filled with the solutions.

Preparation of Solutions of Candidate Solvents Containing Hydrochloric Acid:

4 N hydrochloric acid (0.1 ml) was added to a 100-ml volumetric flask using a measuring pipette, and the 100-ml volumetric flask was filled with various solvents.

Experimental Procedure 2

A 10-mg fraction of Nitto Phase HL comprising dT carried on an aluminum dish obtained via weighing using a balance was added to a 50-ml volumetric flask. The 50-ml volumetric flask was filled with the solvents containing various acid substances prepared in Experimental procedure 1 and the flask was allowed to stand for 7 minutes.

Experimental Procedure 3

After the reaction, polymer beads in the solution were separated via filtration through a filter. The absorbance of the filtrate (412 nm) was determined using a spectrophotometer.
Results:

Deprotection reactivity of DMT groups caused by various solvents in combination with acids was evaluated based on color development. The results of evaluation are summarized in Table 1 below. In Table 1, (*1) shows the results of evaluation using a mixed solution comprising toluene and a solvent at 1:1. In Table 1, the symbol "○" indicates the absorbance within 20%, the symbol "Δ" indicates the absorbance of 50% or lower, and the symbol "x" indicates the absorbance of 5% or lower, in comparison with 3% DCA/toluene.

TABLE 1

| | | Acidic substance | | | | | |
|---|---|---|---|---|---|---|---|
| | | 3% DCA | 3% DCA (*1) | TCA | TFA | PTSA | Hydrochloric acid |
| Candidate solvent | Toluene | ○ | | ○ | | x | |
| | Acetonitrile | x | Δ | ○ | ○ | ○ | ○ |
| | Acetone | x | x | x | | | x |
| | Ethyl acetate | x | x | x | | | x |
| | DMF | x | x | x | | | x |
| | DMSO | x | x | x | | | |
| | Hexane | x | Δ | x | x | | |
| | Methanol | x | x | x | | | |
| | Ethanol | x | x | x | | | |

As shown in Table 1, provided that an acetonitrile solvent was used, acid substances other than DCA were found to have the effects of deprotection equivalent to those achieved with the use of 3% DCA/toluene. In Example 1, trichloroacetic acid (TCA), trifluoroacetic acid (TFA), p-toluenesulfonic acid (PTSA), and hydrochloric acid were subjected to primary screening as alternatives to DCA used for the deprotection reaction.

Example 2

In Example 2, solid-phase nucleic acid synthesis was carried out using trichloroacetic acid (TCA), trifluoroacetic acid (TFA), p-toluenesulfonic acid (PTSA), and hydrochloric acid subjected to primary screening in Example 1 in the step of deprotection, and the purity of the synthesized nucleic acids was evaluated.

Experimental Procedure

In Example 2, nucleic acid synthesis was carried out using an AKTA 10 synthesizer (Amersham Biosciences). A 1.2-ml stainless steel column (diameter: 1 cm; height: 1.5 cm) was used. A nucleic acid sequence to be synthesized was designated as 5'-ATA CCG ATT AAG CGA AGT TT-3' (SEQ ID NO: 1). As a solid-phase support, 350 to 370 μmol/g Nitto Phase HL (Nitto Denko Corporation) was used. In addition, nucleic acid synthesis was carried out by removing a protecting group (a DMT group) from a base at the terminus, and amine wash was carried out using 0.1 N diazabicycloundecene for 30 minutes. As an activator, 5-ethylthio-1-tetrazole (ETT) was used. In Example 2, the step of deprotection was carried out in a reaction column at a linear flow rate of 400 cm/h.

In Example 2, the cleaving reaction was carried out by, at the outset, transferring 50 mg of Nitto Phase HL after the nucleic acid synthesis to a plastic tube with a screw cap. Subsequently, 1 ml of an aqueous solution of 28% ammonia was added to the plastic tube with a screw cap, and the plastic tube was allowed to stand at 55° C. for 16 hours. Thereafter, beads were separated via filtration using 50% ethanol, the reaction product was introduced into a volumetric flask, and the total amount of the content in the volumetric flask was adjusted to 5 mg.

In Example 2, the synthesized nucleic acids were analyzed using an anion exchange column. Specifically, Chromeleon, Thermo Fisher Scientific DNApac PA200 columns (Lot. 014-27-136) were used. The synthesized nucleic acids were identified at the column temperature of 30° C. and at 260 nm. The sample concentration was designated at 1.5 OD/ml and the amount of the sample was designated at 2 μl. As Eluate E1, 20 mM Tris buffer (pH 8.0) was used, and a mixture prepared by adding 1.25 M NaCl (pH 8.0) to Eluate E1 was used as Eluate E2. Eluate E1 and Eluate E2 were supplied to the columns in the manner as shown in Table 2.

TABLE 2

| Time (min) | E1 | E2 |
|---|---|---|
| 0 | 80 | 20 |
| 10 | 55 | 45 |
| 10.1 | 25 | 75 |
| 11.2 | 80 | 20 |
| 14.0 | 80 | 20 |

The results of calculation of the purity of the nucleic acids to be synthesized are shown in Table 3. The purity (%) was calculated in the manner described below. Specifically, a peak area of the target of synthesis was designated as the numerator, the total peak area including the peak arising from impurities was designated as the denominator, and the purity (%) was then calculated.

TABLE 3

| Acid/solvent | Purity (%) |
|---|---|
| 3% DCA/toluene | 87.9 |
| 9% TCA/acetonitrile | 88.3 |
| 5% TFA/acetonitrile | 82.7 |
| p-Toluenesulfonic acid/acetonitrile | 0 (up to 4-mer) |
| HCl/acetonitrile | 0 (up to 3-mer) |

When an acetonitrile solution containing TCA as an acid substance was used, as shown in Table 3, the results of nucleic acid synthesis were equivalent to those attained with the use of a toluene solution containing DCA as an acid substance. When an acetonitrile solution containing TFA as an acid substance was used, also, the results of nucleic acid synthesis were satisfactory.

When the TCA concentration in an acetonitrile solution was 7% or 5%, the results were equivalent to those attained at the TCA concentration of 9%.

When p-toluenesulfonic acid and hydrochloric acid were used as acid substances, however, a nucleic acid having a chain length of interest could not be synthesized.

As is apparent from the results attained in Examples 1 and 2, use of an acid with a pKa of 0.2 to 0.8 (TCA is with a pKa of 0.66 and TFA is with a pKa of 0.2) is sufficient when performing the step of deprotection with the use of an acetonitrile solution. DCA has a pKa of 1.25, p-toluenesulfonic acid has a pKa of −2.8, and hydrochloric acid has a pKa of −8.0.

Example 3

In Example 3, solid-phase nucleic acid synthesis was carried out in the same manner as in Example 2, except that a length of the column used in the reaction of nucleic acid synthesis was increased from 4 cm to 8 cm, and the purity of the synthesized nucleic acids was evaluated. In Example 3, the step of deprotection was carried out using a 3% DCA/toluene solution (linear velocity: 400 cm/h) or a 9% TCA/acetonitrile solution (linear velocity: 800 cm/h).

When a solid-phase support comprising porous resin beads (e.g., Nitto Phase HL) is used, the upper limit of the liquid flow rate is 400 cm/h with the use of a DCA/toluene solution as a deprotection solution for the following reasons. That is, porous resin beads are swollen and softened in a toluene solution, a spherical form cannot be retained due to the pressure applied at a high flow rate, and the flow pass is blocked. When a TCA/acetonitrile solution is used, in contrast, a degree of swelling of porous resin beads in acetonitrile is small, and a spherical form thereof can be maintained at a high flow rate. As a deprotection solution, accordingly, a TCA/acetonitrile solution can be used at the flow rate of 800 cm/h or higher. Example 3 was intended to examine whether or not the duration of acid contact can be shortened and whether or not the purity of nucleic acid synthesis can be improved with the use of a TCA/acetonitrile solution as a deprotection solution at a high flow rate.

The results are shown in Table 4. The purity shown in Table 4 was determined in the same manner as in Example 2.

TABLE 4

| Acid/solvent | Purity (%) | Average deprotection duration (min) |
|---|---|---|
| 3% DCA/toluene | 79.3 | 9.5 ± 2.0 |
| 9% TCA/acetonitrile | 83.5 | 4.7 ± 0.5 |

As shown in Table 4, the purity attained when deprotection was carried out with the use of 3% DCA/toluene according to a conventional technique was 79.3%. That is, such purity was apparently lower than the purity attained when synthesis was carried out with the use of a column with a length of 1.5 cm. Because of an increased column length, specifically, a contact time between a nucleic acid and an acid substance is increased, and the purity is decreased due to the depurination reaction or other reasons. As shown in Table 4, in contrast, a 9% TCA/acetonitrile solution can be used at a high flow rate. Thus, an acid contact time can be shortened, and an increase of 4% or more was observed in purity, compared with the use of a DCA/toluene solution.

In Example 3, the solvents used in Example 1 were quantitatively examined in terms of the effects of swelling in Nitto Phase HL, which is a porous resin bead. Specifically, 1 g of Nitto Phase HL was fractionated, introduced into a 10-ml measuring cylinder, and the cylinder was soaked in the various solvents. The cylinder was allowed to stand overnight, and the volume after swelling was assayed. The results are shown in Table 5.

TABLE 5

| Solvent | Bead weight (g) | Read value (ml) Initial | Read value (ml) Swollen | Degree of swelling (%) |
|---|---|---|---|---|
| Hexane | 1.0002 | 2.68 | 2.90 | 1.08 |
| Methanol | 1.0007 | 2.70 | 3.00 | 1.11 |
| Ethanol | 1.0001 | 2.72 | 3.30 | 1.21 |
| Acetonitrile | 1.0047 | 2.75 | 4.05 | 1.47 |
| Acetone | 1.0002 | 2.70 | 5.61 | 2.08 |
| Ethyl acetate | 1.0016 | 2.72 | 6.00 | 2.21 |
| Toluene | 1.0011 | 2.71 | 6.00 | 2.21 |
| DMF | 1.0000 | 2.70 | 6.96 | 2.58 |
| DMSO | 1.0005 | 2.70 | 9.60 | 3.56 |

As shown in Table 5, porous resin beads were quantitatively found to be less likely to swell in acetonitrile, compared with toluene.

All publications, patents, and patent applications cited herein are incorporated herein by reference in their entirety.

The invention claimed is:

1. A method of solid-phase nucleic acid synthesis in which protected nucleoside phosphoramidites in which a protective group is bonded to a hydroxyl group at the 5' position or the 3' position of a nucleoside are sequentially bound on a solid phase carrier, comprising deprotection of the hydroxyl group by removing the protecting group from the protected nucleoside phosphoramidite in a solution comprising an acid with a pKa of 0.2 to 0.8 and acetonitrile.

2. The method of solid-phase nucleic acid synthesis according to claim 1, wherein the protecting group is a trityl-based protecting group or a silyl-based protecting group.

3. The method of solid-phase nucleic acid synthesis according to claim 1, wherein the acid is trichloroacetic acid or trifluoroacetic acid.

4. The method of solid-phase nucleic acid synthesis according to claim 1, wherein the solid-phase support comprises porous resin beads.

5. The method of solid-phase nucleic acid synthesis according to claim 4, wherein the step of deprotection is carried out by allowing the solution to flow through a column filled with the porous resin beads.

6. The method of solid-phase nucleic acid synthesis according to claim 5, wherein a flow rate of the solution is 400 to 2,000 cm/h.

7. The method of solid-phase nucleic acid synthesis according to claim 5, wherein a length of a layer comprising the porous resin beads introduced into the column is 4 to 50 cm in a flow pass direction, provided that the length is determined when the porous resin beads are swollen with the solution.

* * * * *

UNITED STATES PATENT AND TRADEMARK OFFICE
CERTIFICATE OF CORRECTION

Page 1 of 2

PATENT NO. : 11,692,006 B2
APPLICATION NO. : 16/627718
DATED : July 4, 2023
INVENTOR(S) : Masafumi Iwamoto et al.

It is certified that error appears in the above-identified patent and that said Letters Patent is hereby corrected as shown below:

On the Title Page

Column 2, Line 9, under Abstract, delete "5'position" and insert --5' position--.

In the Specification

In Column 1, Line 24, delete "dimethoxytrytyl" and insert --dimethoxytrityl--.

In Column 1, Line 48, delete "lyophillization," and insert --lyophilization,--.

In Column 2, Line 65, delete "5 'position" and insert --5' position--.

In Column 3, Line 5 (Approx.), delete "trytyl" and insert --trityl--.

In Column 3, Lines 30-31 (Approx.), delete "5 'position" and insert --5' position--.

In Column 4, Line 3, delete "phophodiester" and insert --phosphodiester--.

In Column 4, Line 15, delete "phophodiester" and insert --phosphodiester--.

In Column 5, Line 4, delete "dimethyltrytyl" and insert --dimethyltrityl--.

In Column 5, Lines 6-7, delete "dimethyltrytyl" and insert --dimethyltrityl--.

In Column 5, Line 8, delete "dimethyltrytyl" and insert --dimethyltrityl--.

In Column 5, Line 38, delete "trytyl" and insert --trityl--.

In Column 5, Line 41, delete "trytyl," and insert --trityl,--.

Signed and Sealed this
Thirty-first Day of October, 2023

Katherine Kelly Vidal
*Director of the United States Patent and Trademark Office*

CERTIFICATE OF CORRECTION (continued)
U.S. Pat. No. 11,692,006 B2

In Column 5, Line 45, delete "trytyl" and insert --trityl--.

In Column 5, Line 49, delete "trytyl" and insert --trityl--.

In Column 5, Line 49, delete "trytyl" and insert --trityl--.

In Column 5, Line 50, delete "trytyl" and insert --trityl--.

In Column 5, Line 51, delete "trytyl" and insert --trityl--.

In Column 5, Line 51, delete "trytyl" and insert --trityl--.

In Column 5, Line 53, delete "trytyl" and insert --trityl--.

In Column 5, Line 55, delete "trytyl" and insert --trityl--.

In Column 8, Line 62, delete "column" and insert --column.--.

In Column 10, Line 25, delete "Example 11" and insert --Example 1--.

In Column 10, Line 28, delete "dimethyltrytyl" and insert --dimethyltrityl--.

SEQUENCE LISTING

<160> NUMBER OF SEQ ID NOS: 1

<210> SEQ ID NO 1
<211> LENGTH: 20
<212> TYPE: DNA
<213> ORGANISM: Artificial
<220> FEATURE:
<223> OTHER INFORMATION: Synthetic DNA

<400> SEQUENCE: 1
ataccgatta agcgaagttt                    20